(12) United States Patent
Edic et al.

(10) Patent No.: US 9,466,134 B2
(45) Date of Patent: Oct. 11, 2016

(54) SYSTEMS AND METHODS FOR MOTION CORRECTION USING MAGNETIC RESONANCE IMAGING INFORMATION

(71) Applicant: General Electric Company, Schenectady, NY (US)

(72) Inventors: Peter Michael Edic, Niskayuna, NY (US); Ge Wang, Loudonville, NY (US)

(73) Assignee: General Electric Company, Niskayuna, NY (US)

( * ) Notice: Subject to any disclaimer, the term of this patent is extended or adjusted under 35 U.S.C. 154(b) by 118 days.

(21) Appl. No.: 14/574,671

(22) Filed: Dec. 18, 2014

(65) Prior Publication Data

US 2016/0180553 A1    Jun. 23, 2016

(51) Int. Cl.
*G06T 7/00* (2006.01)
*G06T 11/00* (2006.01)
*G06T 7/20* (2006.01)

(52) U.S. Cl.
CPC ........... *G06T 11/005* (2013.01); *G06T 7/0012* (2013.01); *G06T 7/204* (2013.01); *G06T 11/008* (2013.01); *G06T 2207/10081* (2013.01); *G06T 2207/10088* (2013.01); *G06T 2207/30048* (2013.01)

(58) Field of Classification Search
CPC ......... G06T 5/50; G06T 7/0022; G06T 7/20; G06T 11/005; G06T 11/008; G06T 2207/10081; G06T 2207/10088; G06T 2207/20201; G06T 2207/30048; A61B 5/055; A61B 6/503; A61B 6/5229; A61B 6/5247; A61B 6/5264; G01R 33/4812; G01R 33/563; G01R 33/56308; G01R 33/56509
See application file for complete search history.

(56) References Cited

U.S. PATENT DOCUMENTS

| | | | |
|---|---|---|---|
| 4,580,219 A | 4/1986 | Pelc et al. | 364/414 |
| 8,345,821 B2 | 1/2013 | Sumanaweera et al. | 378/69 |
| 8,469,890 B2 | 6/2013 | Langeland et al. | 600/438 |
| 8,472,683 B2 | 6/2013 | Manjeshwar et al. | 382/128 |
| 8,509,514 B2 | 8/2013 | Chen | 382/131 |
| 8,556,834 B2 | 10/2013 | Gertner | 601/2 |
| 8,568,416 B2 | 10/2013 | Schmitz et al. | 606/79 |
| 2006/0239585 A1 | 10/2006 | Valadez et al. | 382/275 |
| 2009/0149735 A1* | 6/2009 | Fallone et al. | 600/411 |
| 2011/0148928 A1 | 6/2011 | Gopalakrishnan et al. | 345/643 |
| 2012/0265050 A1 | 10/2012 | Wang | 600/441 |
| 2014/0153806 A1* | 6/2014 | Glielmi et al. | G01R 33/481 382/131 |
| 2014/0334702 A1* | 11/2014 | El Fakhri et al. | G06T 11/005 382/131 |

(Continued)

OTHER PUBLICATIONS

Cherry, "Multimodality In Vivo Imaging Systems: Twice the Power or Double the Trouble?", Annual Review of Biomedical Engineering, vol. 8, pp. 35-62, Aug. 2006.

(Continued)

*Primary Examiner* — Andrew W Johns
(74) *Attorney, Agent, or Firm* — Melissa K. Dobson

(57) ABSTRACT

A method of generating an image in one embodiment includes acquiring, with a computed tomography (CT) acquisition unit, CT projection data from at least a region of interest (ROI), and concurrently acquiring, with a magnetic resonance (MR) acquisition unit, MR imaging information of at least a portion of the ROI. The method also includes determining a motion of the at least a portion of the ROI using the MR imaging information, and reconstructing the image using the CT projection data. Reconstructing the image includes motion correcting the CT projection data based on the motion determined using the MR imaging information.

20 Claims, 7 Drawing Sheets

(56) References Cited

U.S. PATENT DOCUMENTS

2014/0355855 A1* 12/2014 Miao et al. ........... G06T 7/2086
  382/131
2015/0230766 A1* 8/2015 Wang et al. ......... A61B 6/4417
  600/411

OTHER PUBLICATIONS

Ge Wang, et al., "Design Proposed for a Combined MRI/Computed-Tomography Scanner," SPIE Biomedical Optics & Medical Imaging, Jun. 11, 2013.).

* cited by examiner

SYSTEMS AND METHODS FOR MOTION CORRECTION USING MAGNETIC RESONANCE IMAGING INFORMATION

BACKGROUND

Imaging information acquired via various imaging modalities (e.g., X-ray computed tomography (CT), positron emission tomography (PET), magnetic resonance imaging (MRI), ultrasound, single photon emission computed tomography (SPECT)) may be combined. It may be desirable to generate complementary imaging data using two or more modalities to take advantage of unique benefits provided by each modality. For example, in some applications, it may desirable to combine complementary CT and MRI imaging information to analyze structures and/or functions from information provided by each modality.

For some imaging applications, for example neural and orthopedic imaging, concurrent or simultaneous acquisition of CT and MRI data is not essential. As such, a patient can be scanned on a CT system and then repositioned for acquisition of MRI data. For example, the patient's anatomy to be scanned may be immobilized and a table registered in both coordinate systems (namely, CT and MR coordinate systems) would be used to facilitate anatomical alignment. Alternatively, rigid and non-rigid motion estimation and correction techniques could be used to register the data. However, patient or organ motion during scanning or collection of imaging data may provide challenges to combining sequentially-acquired CT and MRI information. As one example, cardiac imaging (e.g., imaging of a beating heart) may be subject to motion of the heart during imaging. One conventional approach to minimize effects of a beating heart (or other motion) during CT scanning is to minimize the rotational time (or increase the rotational speed) of CT scanning equipment. However, as rotational speeds increase (and collection time decreases), image quality (e.g., signal-to-noise ratio) may decrease unless higher X-ray flux is provided by the X-ray tube. Further, challenges resulting from motion when imaging in a single modality may be exacerbated when combining sequentially-acquired imaging data from the complementary imaging modalities, as the motion or position of an object being imaged (e.g., the heart) may vary between the different times of imaging using the different modalities.

BRIEF DESCRIPTION

In one embodiment, a method of generating an image is provided including acquiring, with a computed tomography (CT) acquisition unit, CT projection data from at least one of a volume and a region of interest (ROI), and concurrently acquiring, with a magnetic resonance (MR) acquisition unit, MR imaging information of at least a portion of the ROI. The method also includes determining a motion of the at least a portion of the ROI using the MR imaging information, and reconstructing the image using the CT projection data. Reconstructing the image includes motion correcting the CT projection data based on the motion fields determined using the MR imaging information.

In another embodiment, a tangible and non-transitory computer readable medium is provided. The tangible and non-transitory computer readable medium includes one or more computer software modules configured to direct one or more processors to acquire computed tomography (CT) projection data from at least one of a volume and a region of interest (ROI), and to acquire, concurrently with acquiring the CT projection data, MR imaging information of at least a portion of the ROI. The one or more computer software modules are also configured to direct the one or more processors to determine a motion of the at least a portion of the ROI using the MR imaging information, and to reconstruct the image using the CT projection data. Reconstructing the image includes motion correcting the CT projection data based on the motion fields determined using the MR imaging information.

In another embodiment, an imaging system is provided including a computed tomography (CT) acquisition unit, a magnetic resonance (MR) acquisition unit, and a processing unit. The CT acquisition unit has a CT field of view, and is configured to acquire CT projection data from at least one a volume and a region of interest (ROI). The MR acquisition unit has a MR field of view that at least partially overlaps with the CT field of view, and is configured to acquire MR imaging information of at least a portion of the ROI concurrently with acquisition of the CT projection data by the CT acquisition unit. The processing unit is operably coupled to the CT acquisition unit and the MR acquisition unit. The processing unit is configured to determine a motion within the at least a portion of the ROI using the MR imaging information, and to reconstruct an image using the CT projection data, wherein reconstructing the image comprises motion correcting the CT projection data based on the motion field determined using the MR imaging information.

DETAILED DESCRIPTION

Figure 1:
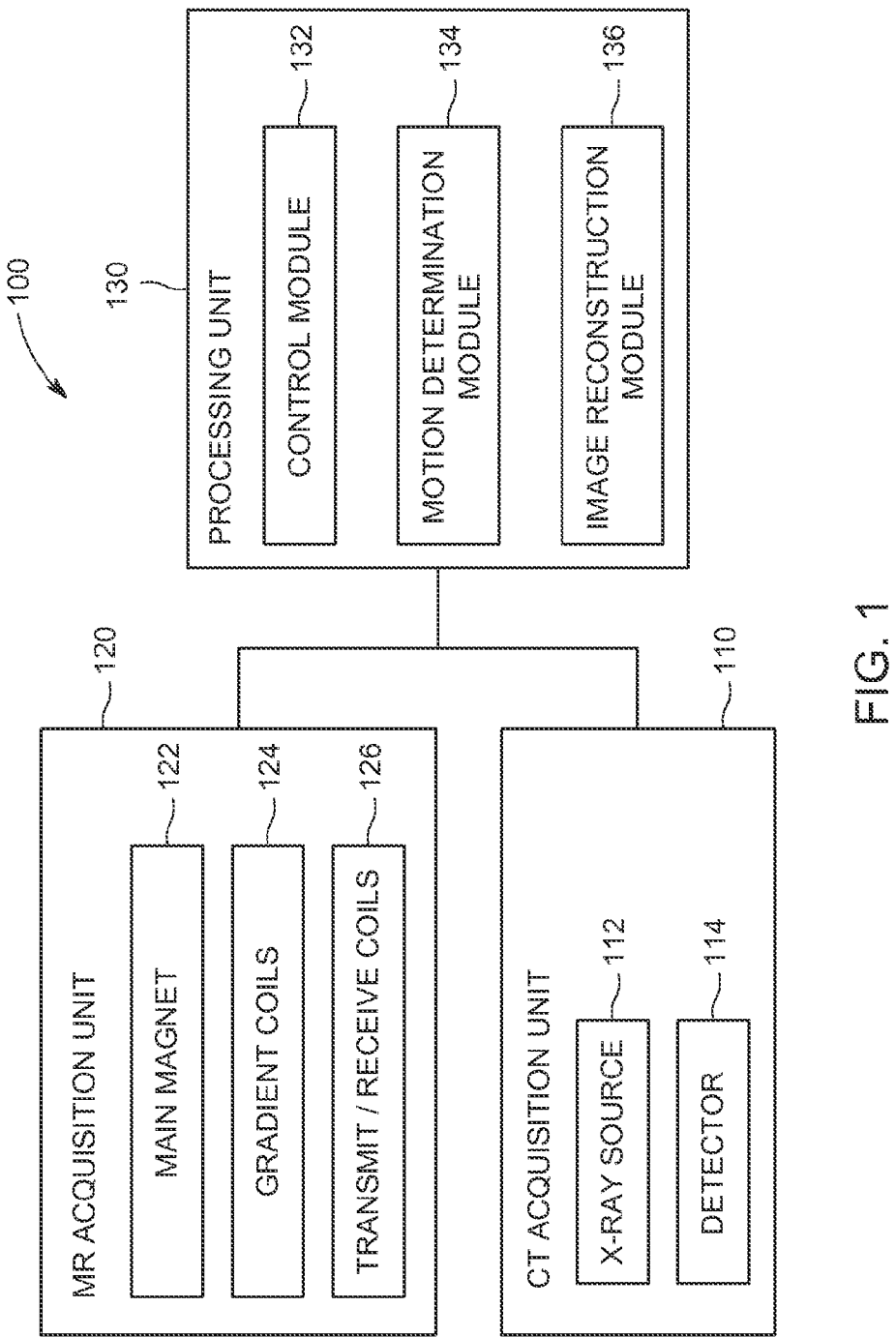
FIG. 1 is a schematic block diagram of an imaging system in accordance with various embodiments.

Various embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, any programs may be stand-alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. The modules or units shown in the attached figures may represent the hardware that operates based on software or hardwired instructions, the software that directs hardware to perform the operations, or a combination thereof. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Generally, various embodiments provide for imaging including motion correction using concurrently acquired MR imaging information and CT projection data. Various systems and/or methods may leverage the complementary benefits of both MR and CT imaging, for example, to improve the fidelity of diagnostic information, and/or to provide complementary information. For example, joint CT-MR systems are currently being investigated (see, for example, Ge Wang, et al., "Design Proposed for a Combined MRI/Computed-Tomography Scanner," SPIE Biomedical Optics & Medical Imaging, Jun. 11, 2013.). The speed and resolution of CT may be combined with the soft tissue sensitivity and molecular imaging capability of MR.

In various embodiments, CT and MR imaging information is acquired concurrently, and the MR imaging information is used to provide motion estimation. In some embodiments, tagged MR imaging may be employed to estimate the motion fields during data acquisition. For example, during a cardiac CT scan, a MR signal in a grid pattern provided within the myocardium may be pre-saturated with radio-frequency (RF) pulses. The grid pattern may be recognizable in MRI images as a dark grid pattern. As the heart cycle progresses during data acquisition, the myocardium contracts and subsequently relaxes. The grid pattern, which is visible in the MRI data, distorts according to the contraction, relaxation, or other movements or processes of a region of interest (e.g., myocardium or portion thereof), thereby providing information regarding motion of the myocardium. For this data, the 3D motion field of the myocardium during the cardiac cycle (or a portion thereof) may be estimated. Based on the movement and/or deformation of the grid, the MR data may be used to estimate a motion field to guide motion-corrected CT image reconstruction. The motion estimates may be used in the CT image reconstruction process to reduce or eliminate motion artifacts and generate data with higher image quality. Various embodiments provide for improved spatial and temporal resolution in CT images (and/or images using fused or combined CT and MR). Various embodiments provide one or more of better quantitation of vessel morphology, plaque composition, myocardial perfusion assessment, or quantitative analysis using computational methods.

In various embodiments, use of concurrently acquired MR imaging information and CT projection data allows acquisition of complementary imaging data. For example, high-resolution anatomical information from CT imaging may be fused with functional and/or molecular information from MR imaging. Further, with concurrently acquired CT projection data being motion corrected during the reconstruction process, the specifications on the rotation speed of the CT gantry (in embodiments using a rotating CT gantry) may be reduced, which has a positive impact on image quality, such as signal-to-noise ratio (SNR), as more photons may be detected per image reconstruction. Reduced rotation speed of the gantry provides system benefits such as reduced complexity of the gantry and reduced power requirements for the X-ray tube. The improved spatial and/or temporal resolution, and/or the improved SNR, may aid in imaging small objects such as coronary artery stenoses, in characterizing constituent components of the plaque comprising the stenosis, in stratifying risk, and/or in providing better estimation of CT perfusion. In various embodiments, the performance of cardiac CT imaging may be improved, for example providing improved ability to stratify patients with coronary artery disease. Put another way, various embodiments provide images or imaging information that may be used to determine for which patients a percutaneous coronary intervention is appropriate and beneficial, for which patients a percutaneous coronary intervention is not needed, for which patients drug therapy is more appropriate, or the like.

At least one technical effect of various embodiments includes improved temporal and/or spatial resolution in CT images (e.g., using improved motion detection and correction techniques). At least one technical effect of various embodiments includes improved SNR in measured projection data and reconstructed imaging data (e.g., via reduced gantry rotation speed and/or eliminated or reduced gantry rotation). At least one technical effect of various embodiments includes improved quantitation of stenosis severity in coronary vessels and/or improved predictive value of cardiac CT for coronary artery disease diagnosis. At least one technical effect of various embodiments includes improved quantitation for cardiac perfusion. At least one technical effect of various embodiments includes reduced hardware constraints of CT system design. At least one technical effect of various embodiments includes higher fidelity CT data for computational fluid dynamics, and/or improved fidelity of hemodynamic parameter estimation (e.g., computational fractional flow reserve or coronary flow reserve).

FIG. 1 is a schematic block diagram of an imaging system 100 in accordance with various embodiments. The depicted imaging system 100 includes a computed tomography (CT) acquisition unit 110, a magnetic resonance (MR) acquisition unit 120, and a processing unit 130. Generally, the CT acquisition unit 110 and the MR acquisition unit 120 are configured to concurrently obtain imaging information from at least one of a volume and a region of interest, and the processing unit 130 is configured to obtain the imaging information from the CT acquisition unit 110 and the MR acquisition unit 120, to determine a motion field using imaging information from the MR acquisition unit 120, and to reconstruct an image, based on the determined motion field, using at least imaging information from the CT acquisition unit 110. It may be noted that the particular components or sub-components, such as units or modules shown in FIG. 1 are meant by way of example, and that other arrangements of units or sub-units of the CT acquisition unit 110, MR acquisition unit 120, and/or processing unit 130 may be employed in various embodiments.

The depicted CT acquisition unit 110 includes an X-ray source 112 and a detector 114. Generally, X-rays from the X-ray source 112 pass through an object (and are attenuated by the object as the X-rays pass through the object, not shown) and are received by the detector 114. Based on the attenuation of the X-rays received by the detector 114, an image of the object may be reconstructed. By providing X-rays across a range of slices taken at different azimuthal angles or view positions surrounding an object (e.g., a range of azimuthal angles that is sufficient for image reconstruction), and combining the information from each of the slices, a 3-dimensional image representing interior features of the object may be provided. Various different configurations of CT acquisition unit 110 may be employed in various embodiments. For example, in some embodiments, a single X-ray source and corresponding detector may be rotated about a bore of a gantry within which an object to be imaged is disposed. In some embodiments, multiple X-ray sources and/or detectors (rotating or non-rotating) may be employed. As one more example, in some embodiments, an electron beam may be employed. For example, an electron beam may be swept across a distributed anode comprising an angular range, such as an angular coverage sufficient for image reconstruction, surrounding an object to be imaged.

The depicted MR acquisition unit 120 includes a main magnet 122, gradient coils 124, and transmit/receive coils 126. Generally, a main magnetic field is provided by the main magnet 122, which may be a superconducting magnet. The gradient coils 124 are disposed within the field of the main magnet 122, and may be employed to vary the main magnetic field. The gradient coils 124 may be employed to produce smaller amplitude, spatially varying magnetic fields when a current is applied to the gradient coils 124. When a portion of the human body is placed in the main magnetic field, the nuclear spins that are associated with hydrogen nuclei in tissue water become polarized, and the magnetic moments that are associated with the spins become preferentially aligned along the direction of the main magnetic field, resulting in a small net tissue magnetization along the main magnetic field. The transmit/receive coils 126 (which may be configured as separate transmit coils and receive coils in various embodiments) are connected to a radio-frequency (RF) transmitter and/or receiver, and controlled so that RF pulses or signals are generated and applied to the patient for excitation of unpaired hydrogen nuclei (excess hydrogen nuclei in the spin-up state) in the patient. Various different configurations of MR acquisition unit 120 may be employed in various embodiments. It may be noted that, in some embodiments, the MR acquisition unit 120 may utilize relatively smaller magnetic fields to help reduce issues of placement of the CT acquisition unit 110 within the magnetic fields. (For a general description of various aspects of CT and MR systems, see FIGS. 6 and 7, respectively.)

Figure 2:
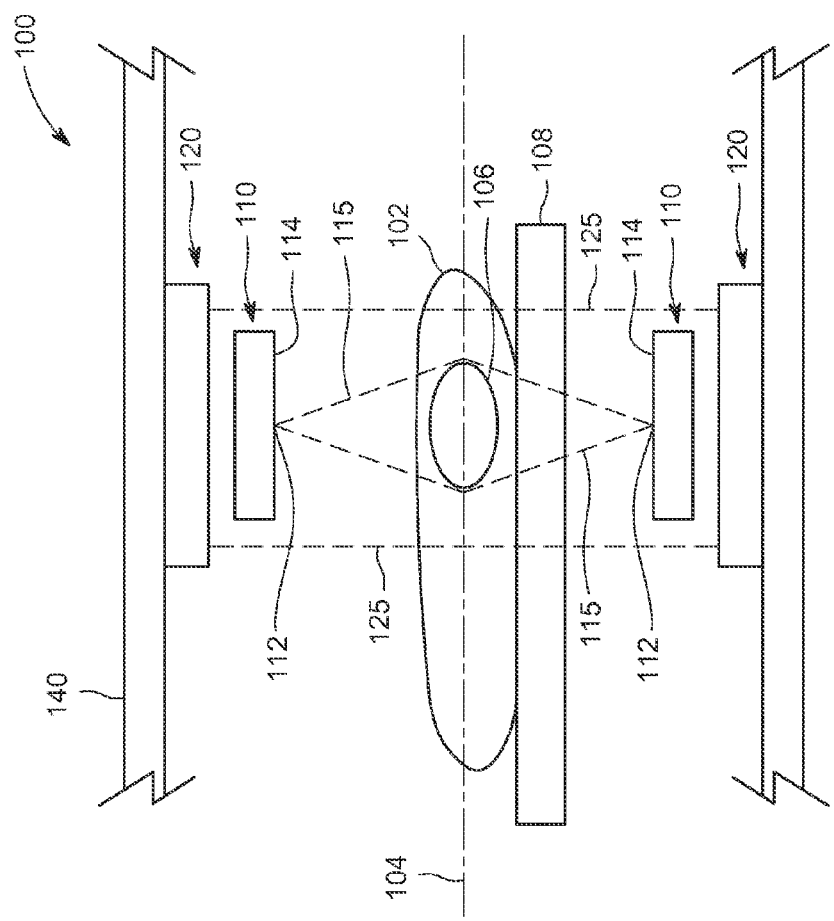
FIG. 2 is a schematic side view of the imaging system of FIG. 1 in accordance with various embodiments.
Figure 3:
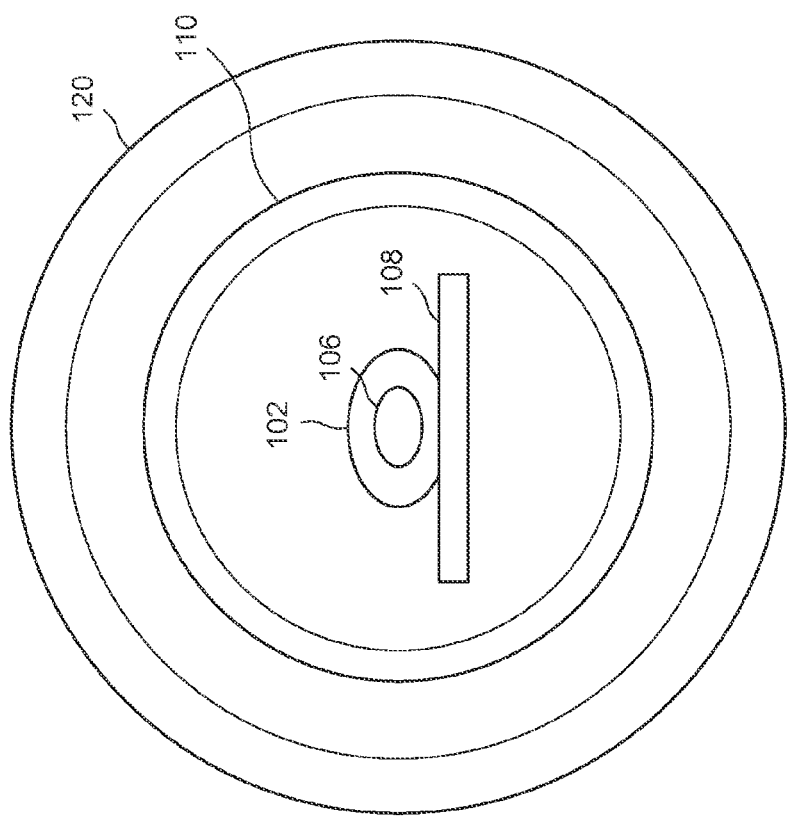
FIG. 3 is a schematic end view of the imaging system of FIGS. 1 and 2 in accordance with various embodiments.

As indicated above, different configurations and/or arrangements of the acquisition units may be employed in various embodiments. By way of example, FIGS. 2 and 3 depict schematic side and end cross-sectional views, respectively, of the imaging system 100 in accordance with various embodiments. (The processing unit 130 is not shown in FIGS. 2 and 3 for ease and clarity of illustration.) It may be noted that other types of acquisition units and/or other arrangements of acquisition units may be employed in various embodiments. For example, in some embodiments, the CT acquisition unit 110 and the MR acquisition unit 120 may be offset from each other along the longitudinal axis 104 and/or disposed at an angle with respect to each other. It should be noted that FIGS. 2 and 3 are schematic in nature and provided for ease of illustration and explanation, and are not intended to impose any limits or restrictions on system topology.

The imaging system 100 depicted in FIGS. 2 and 3 includes the CT acquisition unit 110 and the MR acquisition unit 120 disposed within a housing or gantry 140. A support 108 (e.g., table, bed, cradle, or the like) is disposed within the gantry 140, and is configured to support an object 102 along a longitudinal axis 104. The object 102 may be, for example, a human patient, and includes a region of interest 106. The region of interest 106 may be a portion of a human patient, such as a heart and/or surrounding tissue. The imaging system 100 is configured to acquire scanning or imaging information of the region of interest 106. In the embodiment depicted in FIG. 2, the X-ray source 112 of the CT acquisition unit 110 emits from at least one X-ray source location along an axis perpendicular to the longitudinal axis 104. For example, the X-ray source 112 may produce X-ray flux disposed generally centrally with respect to one or more detectors 114. When considering the imaging volume resulting from projection data comprising an angular coverage of 360 degrees about the patient, the CT acquisition unit 110 may generate an illumination volume 115 that is larger toward a center of a bore of the gantry 140 than the illumination volume 115 proximate the detector 114. In the embodiment depicted in FIG. 2, the MR acquisition unit 120 has a differently shaped field of view 125 that is also larger than the illumination volume 115 of the CT acquisition unit 110. Both the illumination volume 115 of the CT acquisition unit 110 and the field of view 125 of the MR acquisition unit 120 are configured to include at least the region of interest 106. One or both fields of view may include additional tissue or material of the object 102. In various embodiments, for example embodiments where the CT acquisition unit 110 and the MR acquisition unit 120 are offset from each other along the longitudinal axis 104, other shapes, sizes, and/or arrangements of fields of view may be utilized.

In the depicted example, as best seen in FIG. 3, the CT acquisition unit 110 is disposed concentrically with the MR acquisition unit 120 and within an outer radial boundary of the MR acquisition unit 120. The outer radial boundary of the MR acquisition unit may be defined at least in part by a main magnet, such as a superconducting magnet. Again, it should be noted that the arrangement provided in FIG. 3 is schematic in nature and presented for illustrative purposes only. Other arrangements may be provided in other embodiments. For example, one or more portions of the MR acquisition unit 120 (e.g., transmit and/or receive coils) may be within a radial boundary of the CT acquisition unit 110. For example proposed design topologies combining CT and MR acquisition units, see Ge Wang, et al., "Design Proposed for a Combined MRI/Computed-Tomography Scanner," SPIE Biomedical Optics & Medical Imaging, Jun. 11, 2013.

Returning to FIG. 1, the processing unit 130 includes a control module 132, a motion determination module 134, and an image reconstruction module 136. The processing unit 130 may include processing circuitry configured to perform one or more tasks, functions, or steps discussed herein. In various embodiments, the processing unit 130 may be configured to obtain CT projection data and MR imaging information, determine a motion field within at least a portion of an ROI using the MR imaging information, and to reconstruct an image using the CT projection data and the motion field determined using the MR imaging information. The particular arrangement of units or modules shown in FIG. 1 is schematic in nature and meant by way of example for illustrative purposes. Other arrangements of units or modules of the processing unit 130 may be employed in various embodiments. For example, one or more aspects of a given depicted module may be provided in a separate module and/or shared with an additional module, aspects of depicted modules may be shared or combined in a common module, or the like. Further, it may be noted that one or more modules (or aspects thereof) need not necessarily be disposed within a common physical unit with other modules. For example, aspects of the control module 132 may be disposed or positioned with the CT acquisition unit 110 and/or the MR acquisition unit 120.

The depicted control module 132 is configured to control the operation of the CT acquisition unit 110 and the MR acquisition unit 120. For example, the control module 132 may control the CT acquisition unit 110 and the MR acquisition unit 120 to collect, gather, or acquire imaging information over concurrent time frames. By collecting information over concurrent time frames, motion present in an object being imaged will be represented similarly in both the CT projection data and the MR imaging information acquired. A motion determined using one of the modalities (e.g., MR) may be used to correct motion or account for motion of the other modality (e.g., CT) when reconstructing an image. In some embodiments, the time frames of image information collection may entirely overlap with each other, while in other embodiments, the time frames of image information collection may partially overlap (e.g., information for one modality may be collected over a longer time period than for another modality). Further still, in other embodiments, the time frames of image information collection may have no overlap.

The depicted motion determination module 134 is configured to estimate or otherwise determine a motion field within at least a portion of an ROI being imaged during data acquisition using MR image information acquired via the MR acquisition unit 120. As the MR image information is acquired concurrently with the CT image information, motion fields determined using the MR image information may be directly applied, considered, or accounted for when reconstructing an image using the CT image information during the corresponding time. The MR image information (and/or motion field information determined using the MR image information) and the CT image information, for example, may be associated with time stamps or other marks or labels indicating that the information was obtained during a common time interval.

It may be noted that the time required to acquire clinically or diagnostically useful CT information may be less in some embodiments than the time required to acquire clinically or diagnostically useful MR information and/or to acquire MR information sufficient to describe motion within an entire ROI. In various embodiments, the time to acquire MR information may be reduced to equal the time used to acquire CT information or more closely approach the time used to acquire the CT information. For example, motion may be estimated using information from a portion of the ROI and used to estimate motion for one or more remaining portions of the ROI, reducing the amount of information required (and the time to require the information). Thus, in some embodiments, a region of interest may include a portion for which motion has been determined using MR information and at least one additional portion for which motion has not been determined directly or measured using MR information, with the processing unit 130 configured to estimate a motion field within the ROI (e.g., including the at least one additional portion for which motion has not been determined directly using MR information) based on the measured or directly determined motion field within the portion of the ROI.

Additionally or alternatively, the time used to acquire MR information may be reduced by collecting MR information at a resolution that is lower than the highest imaging resolution capability. (As used herein, an imaging resolution may be understood as a resolution that provides a clinically useful image using a single modality). For example, if the MR information is used solely for motion determination, the MR information may be acquired at a lower resolution than standard CT imaging resolution for a MR imaging application, reducing the amount of time required to collect the MR information (and/or reducing equipment specifications or requirements for acquiring the MR information). As another example, if the MR information is used in conjunction with CT information, the MR information may be acquired at a lower resolution than for an application for imaging using MR alone, thereby reducing the amount of time required to collect the MR information (and/or reducing equipment specifications or requirements for acquiring the MR information).

Figure 4:
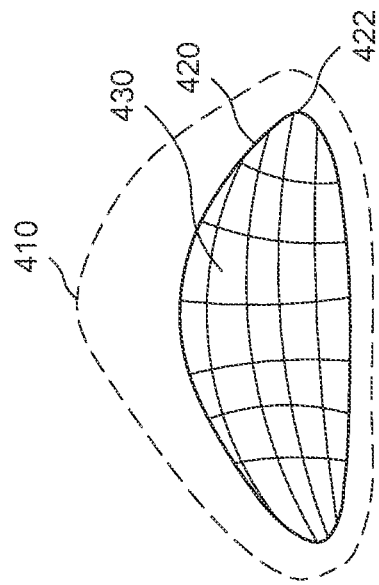
FIG. 4 illustrates motion determination and estimation of a "tagged" object in accordance with various embodiments.
Figure 4:
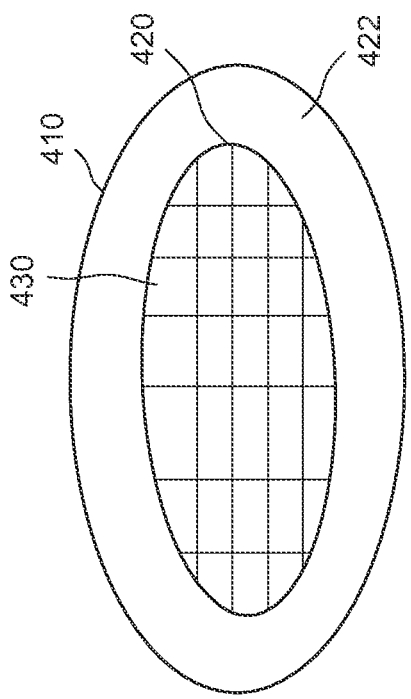

FIG. 4 provides a schematic depiction of an example of motion field estimation in accordance with various embodiments. In FIG. 4, a region of interest 410 is shown in an initial position 402 and in a subsequent, motion-affected position 404. A technique referred to as "tagging" is used in conjunction with the example of FIG. 4. In MR imaging tagging, a MR signal in a grid pattern may be provided on an object (or portion thereof). The grid pattern may be generated by pre-saturating the tissue with radio-frequency (RF) pulses, and may be recognizable in MR images as a dark grid pattern. A magnetization gradient or magnetic field may be controlled to provide the grid pattern. For example, the control module 132 may control the MR acquisition unit 120 to provide the grid pattern on at least a portion of an ROI of the object. As the object (or portion thereof) moves during data acquisition, the grid pattern, which is visible in the MRI data, distorts according to the motion, thereby providing information regarding motion within at least a portion of the ROI. By determining the distortion or movement of the grid pattern, the movement of the corresponding or "tagged" portion may be determined or estimated.

For example, as seen in FIG. 4, the illustrated region of interest 410 includes a tagged portion 420 and an additional (or non-tagged) portion 422. A grid 430 is provided on the tagged portion 420 using MR signals. As the region of interest 410 distorts from the initial position 402 to the motion-affected position 404 (indicated in dashed line), the tagged portion 420 distorts a corresponding amount. The grid 430 on the tagged portion 420 distorts, so that the changes in the grid 430 may be determined and used to determine the change (or motion) of the tagged portion 420. The motion of the tagged portion 420 may in turn be utilized to determine the motion field within the depicted region of interest 410. (It may be noted that, depending, for example, on the shape of the region of interest 410, the shape of the tagged portion 420, and/or the extent or shape of the distortion or movement of the region of interest 410, the exact distortion of the tagged portion 420 may differ somewhat from the distortion of the region of interest 410, but be similar enough so that the distortion of the region of interest 410 may be estimated or extrapolated based on the distortion of the tagged portion 420.)

It may be noted that the depiction of FIG. 4 is schematic in nature, and that the relationship between the tagged portion 420 and the additional portion 422 may differ in various embodiments. In some embodiments, the additional (or non-tagged) portion 422 may be disposed on or near a surface of the tagged portion 420. For example, in some embodiments, the tagged portion 420 may include the myocardium of a heart (or portion thereof), and the additional portion 422 may include vessels disposed along or near a surface of the myocardium. In various alternative embodiments, the tagged portion 420 may comprise the entire region of interest 410.

Returning to FIG. 1, the depicted image reconstruction module 136 is configured to reconstruct an image using the CT projection data. The image reconstruction module 136 in various embodiments uses motion fields estimated using the MR imaging information (e.g., motion field estimated by the motion determination module 134) to reconstruct the image. The image reconstruction module 136 may, for example, use one or more conventional motion correction techniques to account for the motion field estimated by the motion determination module 134 when reconstructing the image. Further, in some embodiments, the image reconstruction module may employ MR imaging information acquired by the MR acquisition unit 120 to reconstruct an image. Thus, the MR imaging information may be used to complement acquired CT projection data as well as for determining motion. In various embodiments, high-resolution anatomical information from CT imaging may be fused with functional and/or molecular information from MR imaging information to provide improved diagnostic capability.

Figure 5:
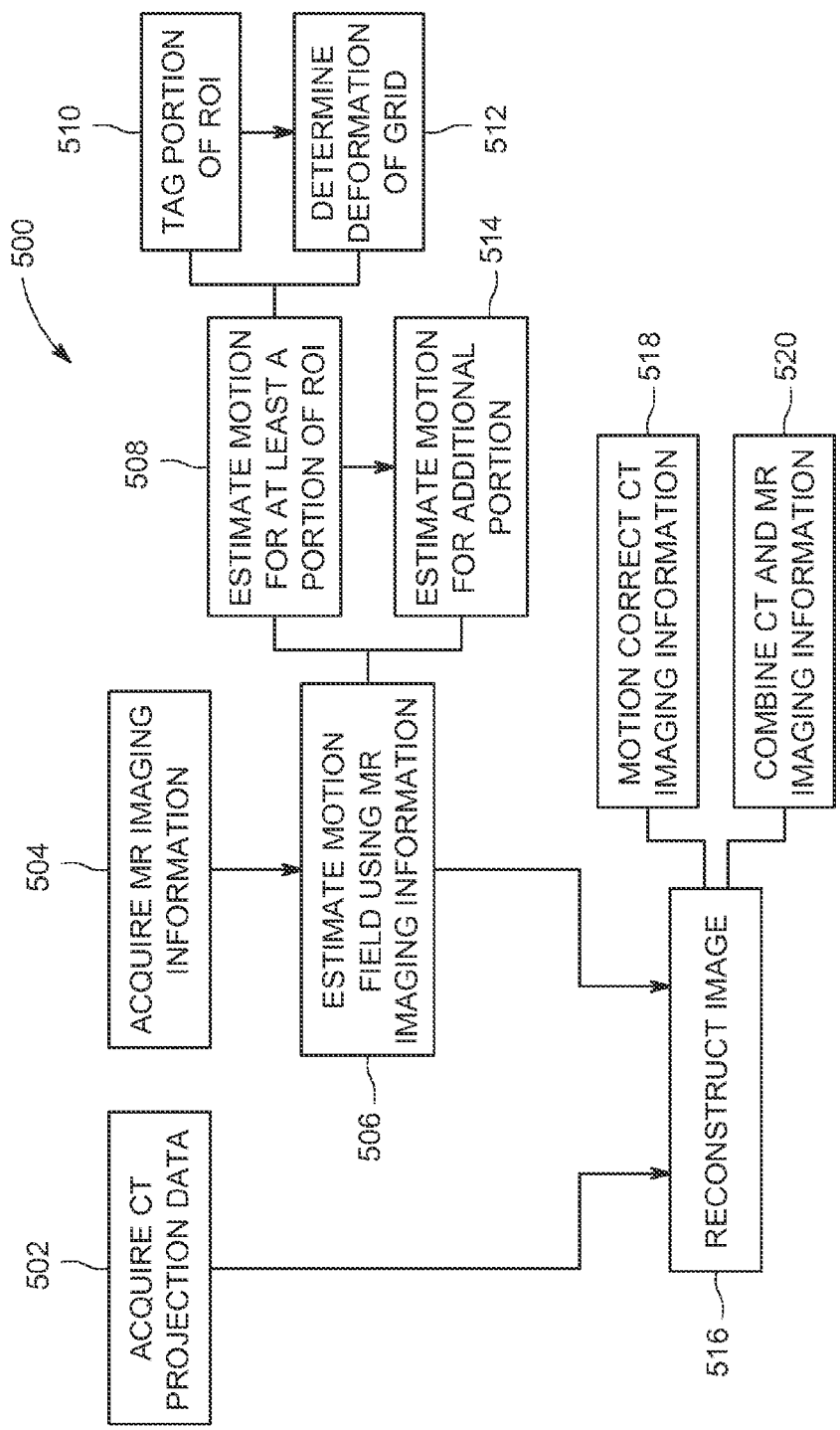
FIG. 5 is a flowchart of a method for generating an image in accordance with various embodiments.

FIG. 5 provides a flowchart of a method 500 for generating or providing an image of an object (e.g., an image comprising a least one of a volume or a region of interest of an object that may be affected by motion). In various embodiments, the method 500, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 500 may be able to be used as one or more algorithms to direct hardware to perform operations described herein.

At 502, CT projection data is acquired (e.g., via CT acquisition unit 110 of imaging system 100). One or more X-ray sources may provide X-ray flux that passes through an object and is collected by one or more detectors. The attenuation of the X-rays as the X-rays pass through the object may be used to generate an image of the object. At 504, MR imaging information is acquired (e.g., via MR acquisition unit 120 of imaging system 100). In the depicted embodiment, the CT projection data and the MR imaging information are acquired concurrently. The MR and CT imaging information may be correlated or associated with each other, for example, via time stamps, so that information from a same point or range of time may be associated or correlated (e.g., for motion correction and/or for complementary imaging). With the MR and CT imaging information acquired concurrently or simultaneously, motion of an object being imaged is similar for or common to both sets of information. Put another way, the concurrently or simultaneously collected MR and CT information are each similarly or correspondingly affected by motion of an object or ROI being imaged.

At 506, a motion field is estimated using the MR imaging information. For example, motion in MR imaging may be determined using tagging or use of a signal-saturated grid of MR signals provided on an object or portion thereof. The deformation of the grid is observed, monitored, or measured from the MR imaging information to determine the deformation or motion of the associated object or portion thereof. In some embodiments, the motion may be measured or directly determined for an entire object or entire ROI. In other embodiments, for example to reduce acquisition time and/or equipment requirements, motion may be determined directly or measured for a portion of an ROI, and estimated for the remainder or additional portions of the ROI.

For example, at 508, a motion field is estimated for at least a portion of the ROI. The motion field may be estimated using a tagging technique as discussed herein. The motion field of the at least a portion of the ROI may be determined using sub-steps as shown in FIG. 5. At 510, a portion of the ROI is tagged, and, at 512, the deformation of a grid associated with the portion of the ROI is determined, with the motion of the portion of the ROI determined based on the deformation or motion of the grid. For example, for a cardiac scan, the myocardium (or a portion thereof) may be tagged and the motion determined for the myocardium (or portion thereof) based on the deformation or movement of a grid associated with the myocardium as part of a tagging process.

With the motion for the portion of the ROI determined (e.g., at 508), at 514, the motion for one or more additional portions of the ROI are estimated. For example, with motion of a myocardium determined, the motion of vessels along or near one or more surfaces of the myocardium may be estimated, for example, based on the position of the vessels with respect to the myocardium at an initial or reference position.

At 516, the image is reconstructed using CT projection data obtained at 502. The CT projection data may be motion corrected at 518 using the motion field determined at 506 using the MR imaging information. In some embodiments, the image may be a CT image reconstructed using CT projection data obtained at 502 that is motion corrected based on MR imaging information obtained at 504. In other embodiments, the reconstructed image may utilize both CT and MR imaging information. For example, at 520, the CT and MR imaging information may be combined or fused in generating the image. In some embodiments, high-resolution anatomical information from CT imaging may be fused with functional and/or molecular information from MR imaging information to provide a fused or combined image providing improved diagnostic capability.

Figure 6:
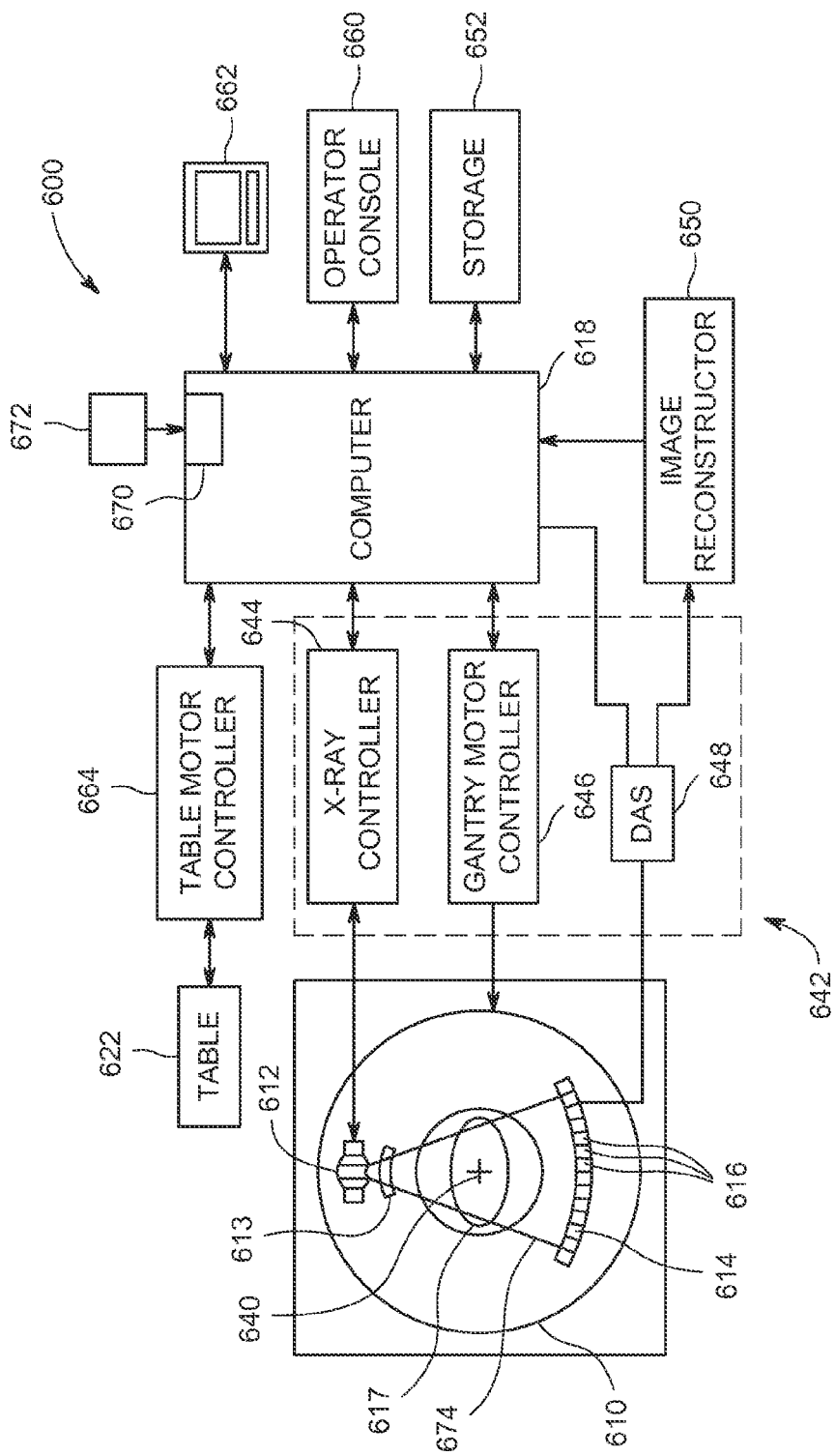
FIG. 6 is a schematic view of a CT imaging system in accordance with various embodiments.

FIG. 6 provides a general description of a CT imaging system illustrating certain general concepts of CT imaging that may be employed in various embodiments. In FIG. 6, a CT imaging system 600 includes a gantry 610 that has an X-ray source 612 that projects a beam of X-rays toward a multi-slice detector array 614 on the opposite side of the gantry 610. A source collimator 613 is provided proximate to the X-ray source 612. The multi-slice detector array 614 includes a plurality of detector elements 616 that are arranged in rows and columns that together sense the X-rays that pass through or bypass a subject 617. The imaging system 600 also includes a computer 618 that receives the projection data from the multi-slice detector array 614 via a data acquisition system (DAS) 648, and processes the projection data to reconstruct an image of the subject 617. The computer 618, for example, may include one or more aspects of the processing unit 130, or be operably coupled to one or more aspects of the processing unit 130. In operation, operator supplied commands and parameters via an operator console 660 are used by the computer 618 to provide control signals and information to reposition a motorized table 622. More specifically, the motorized table 622 is utilized to move the subject 617 into and out of the gantry 610. Particularly, the table 622 moves at least a portion of the subject 617 through a gantry opening that extends through the gantry 610. Further, the table 622 may be used to move the subject 617 vertically within the bore of the gantry 610.

As discussed above, the multi-slice detector 614 includes a plurality of detector elements 616. Each detector element 616 produces an electrical signal, or output, that represents the intensity of an impinging X-ray beam and hence allows estimation of the line integral of the attenuation of the beam as it passes through the subject 617. During a scan to acquire the X-ray projection data, the gantry 610 and the components mounted thereon rotate about a center of rotation 640. FIG. 6 shows only a single row of detector elements 616 (i.e., a detector row). However, the multi-slice detector array 614 includes a plurality of parallel detector rows of detector elements 616 such that projection data corresponding to a plurality of slices can be acquired simultaneously during a scan.

Rotation of the gantry 610 and the operation of the X-ray source 612 are governed by a control mechanism 642. The control mechanism 642 includes an X-ray controller 644 that provides power and timing signals to the X-ray source 612 and a gantry motor controller 646 that controls the rotational speed and position of the gantry 610. The data acquisition system (DAS) 648 in the control mechanism 642 samples analog data from detector elements 616 and converts the data to digital signals for subsequent processing. An image reconstructor 650 receives the sampled and digitized X-ray data from the DAS 648 and performs high-speed image reconstruction. The reconstructed images are input to the computer 618 that stores the image in a storage device 652. The computer 618 may also receive projection data from multi-slice detector 614, as well as commands and scanning parameters from an operator via the console 660 (e.g., via a keyboard or other input device of the console 660). An associated visual display unit 662 allows the operator to observe the reconstructed image and other data from computer. It may be noted that one or more of the computer 618, controllers, or the like may be incorporated as part of a processing unit such as the processing unit 130 discussed herein.

The operator supplied commands and parameters are used by the computer 618 to provide control signals and information to the DAS 648, the X-ray controller 644 and the gantry motor controller 646. In addition, the computer 618 operates a table motor controller 664 that controls the motorized table 622 to position the subject 617 in the gantry 610. Particularly, the table 622 moves at least a portion of the subject 617 through the gantry opening.

In various embodiments, the computer 618 includes a device 670, for example, a CD-ROM drive, DVD drive, magnetic optical disk (MOD) device, or any other digital device including a network connecting device such as an Ethernet device for reading instructions and/or data from a tangible non-transitory computer-readable medium 672, such as a CD-ROM, a DVD or another digital source such as a network or the Internet, as well as yet to be developed digital means. In another embodiment, the computer 618 executes instructions stored in firmware (not shown). The computer 618 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the X-ray source 612 and the multi-slice detector array 614 are rotated with the gantry 610 within the imaging plane and around the subject 617 to be imaged such that the angle at which an X-ray beam 674 intersects the subject 617 constantly changes. A group of X-ray attenuation measurements, i.e., projection data, from the multi-slice detector array 614 at one gantry angle is referred to as a "view". A "scan" of the subject 617 comprises a set of views made at different gantry angles, or view angles, during one or more revolutions of the X-ray source 612 and the multi-slice detector 614. In a CT scan, the projection data is processed to reconstruct an image that corresponds to a three-dimensional volume taken of the subject 617. It may be noted that, in some embodiments, an image may be reconstructed using less than a full revolution of data. For example, with a multi-source system, substantially less than a full rotation may be utilized. Thus, in some embodiments, a scan (or slab) corresponding to a 360 degree view may be obtained using less than a complete revolution. Moreover, in some embodiments, 2 or more X-ray sources 612 and multi-slice detectors 614 may be employed to minimize the gantry rotation needed to acquire CT projection data suitable for image reconstruction.

Figure 7:
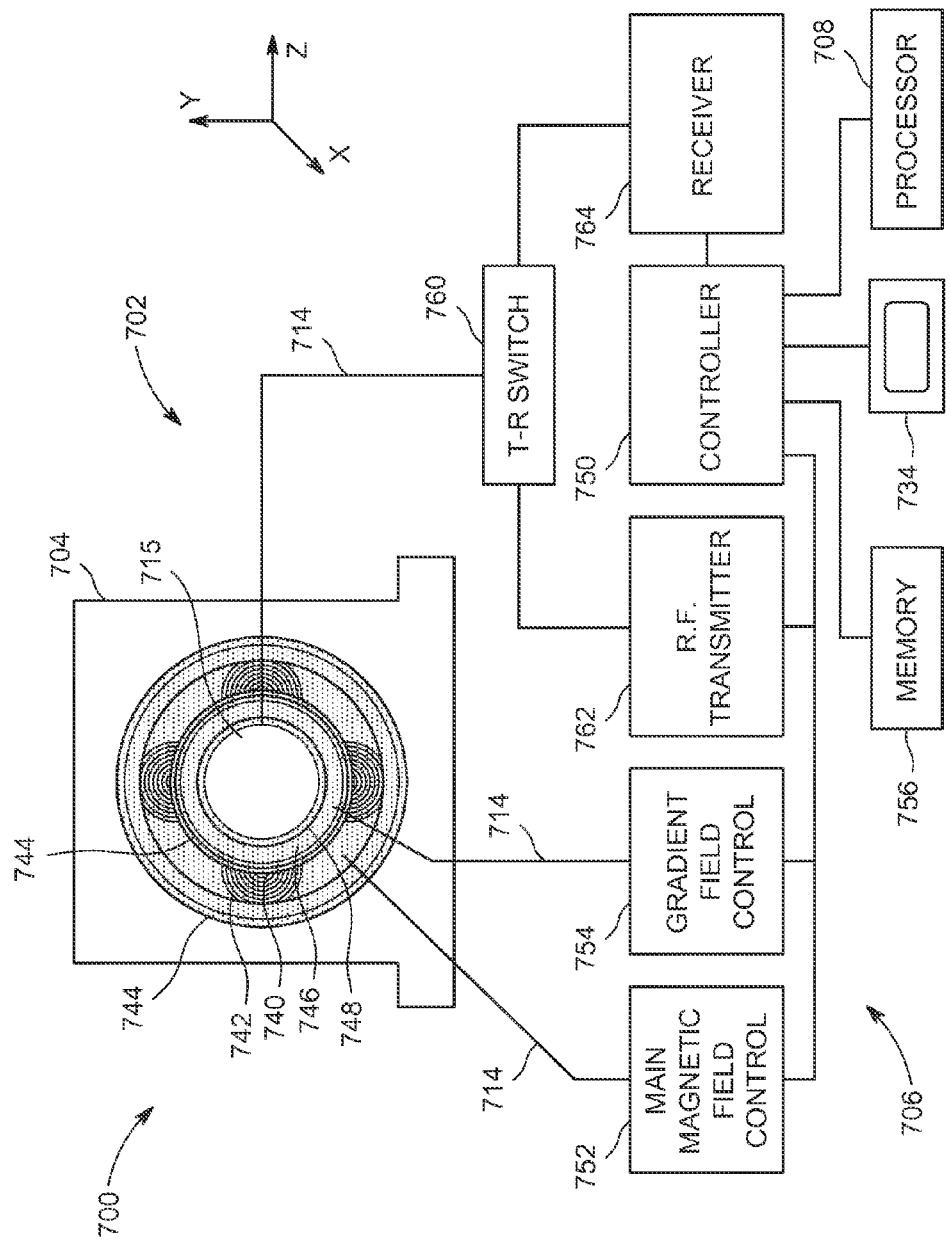
FIG. 7 is a schematic view of an MR imaging system in accordance with various embodiments.

FIG. 7 provides a general description of an MR imaging system illustrating certain general concepts of MR imaging that may be employed in various embodiments. As seen in FIG. 7, an imaging system 700 includes an imaging portion 702 having an imaging unit 704 (e.g., imaging scanner) and a processing portion 706 that may include a processor 708 or other computing or controller device. In particular, the imaging unit 704 enables the imaging system 700 to scan an object or patient to acquire imaging data, which may be imaging data of all or a portion of the object or patient. The imaging unit 704 includes one or more imaging components that allow acquisition of imaging data. The imaging components produce signals that represent imaging data that is communicated to the processing portion 706 via one or communication links 714 that may be wired or wireless. The patient may be positioned within a bore 715.

In operation, an output of one or more of the imaging components is transmitted to the processing portion 706, and vice versa, which may include transmitting signals to or from the processor through a control interface. The processor 708 also may generate control signals for controlling the position of the motorized table and imaging components based on user inputs or a predetermined scan. For example, RF signals or transmit pulses may be communicated through the one or more communication links 714 (e.g., via T-R switch 760).

During a scan, imaging data, such as magnetic resonance imaging data from the imaging components may be communicated to the processor 708 through a data interface via the control interface, for example, as acquired by a body coil or surface coil.

The processor 708 and associated hardware and software used to acquire and process data may be collectively referred to as a workstation. The workstation may include, for example, a keyboard and/or other input devices such as a mouse, a pointer, and the like, and a monitor 734. The monitor 734 displays imaging data and may accept input from a user if a touchscreen is available.

In the exemplary embodiment, the imaging system 700 also includes a superconducting magnet 740 formed from magnetic coils supported on a magnet coil support structure. However, in other embodiments, different types of magnets may be used, such as permanent magnets or electromagnets. A vessel 742 (also referred to as a cryostat) surrounds the superconducting magnet 740 and is filled with liquid helium to cool the coils of the superconducting magnet 740. A thermal insulation 744 is provided surrounding the outer surface of the vessel 742 and the inner surface of the superconducting magnet 740. A plurality of magnetic gradient coils 746 are provided within the superconducting magnet 740 and an RF transmit coil 748 is provided within the plurality of magnetic gradient coils 746. In some embodiments the RF transmit coil 748 may operate as a receive coil. It should be noted that although the superconducting magnet 740 is a cylindrical shape, other shapes of magnets can be used.

The processing portion 706 also generally includes a controller 750, a main magnetic field control 752, a gradient field control 754, a memory 756, the display device 734, a transmit-receive (T-R) switch 760, an RF transmitter 762 and a receiver 764.

In operation, a body of an object, such as the patient or a phantom to be imaged, is placed in the bore 715 on a suitable support, for example, a motorized table or other patient table. The superconducting magnet 740 produces a uniform and static main magnetic field $B_o$ across the bore 715. The strength of the electromagnetic field in the bore 715 and correspondingly in the patient, is controlled by the controller 750 via the main magnetic field control 752, which also controls a supply of energizing current to the superconducting magnet 740.

The magnetic gradient coils 746, which include one or more gradient coil elements, are provided so that a magnetic gradient can be imposed on the magnetic field $B_o$ in the bore 715 within the superconducting magnet 740 in any one or more of three orthogonal directions x, y, and z. The magnetic gradient coils 746 are energized by the gradient field control 754 and are also controlled by the controller 750.

The RF transmit coil 748 is arranged to transmit RF magnetic pulses and/or optionally detect MR signals from the patient if receive coil elements are not provided on the patient. The RF transmit coil 748 is selectably interconnected to one of the RF transmitter 762 or receiver 764, respectively, by the T-R switch 760. The RF transmitter 762 and T-R switch 760 are controlled by the controller 750 such that RF field pulses or signals that are generated by the RF transmitter 762 are selectively applied to the patient for excitation of magnetic resonance in the patient.

Following application of the RF pulses, the T-R switch 760 is again actuated to decouple the RF transmit coil 748 from the RF transmitter 762. The detected MR signals are in turn communicated to the controller 750. The controller 750 includes a processor (e.g., image reconstruction processor), for example the processor 708, that controls the processing of the MR signals to produce signals representative of an image of the patient.

The processed signals representative of the image are also transmitted to the display device 734 to provide a visual display of the image. Specifically, the MR signals fill or form a k-space that is Fourier transformed to obtain a viewable image. The processed signals representative of the image are then transmitted to the display device 734.

It should be noted that the particular arrangement of components (e.g., the number, types, placement, or the like) of the illustrated embodiments may be modified in various alternate embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optic drive, and the like. The storage device may also be other similar means for loading computer programs or other instructions into the computer or processor.

As used herein, the term "computer," "controller," and "module" may each include any processor-based or microprocessor-based system including systems using microcontrollers, reduced instruction set computers (RISC), application specific integrated circuits (ASICs), logic circuits, GPUs, FPGAs, and any other circuit or processor capable of executing the functions described herein. The above examples are exemplary only, and are thus not intended to limit in any way the definition and/or meaning of the term "module" or "computer."

The computer, module, or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, module, or processor as a processing machine to perform specific operations such as the methods and processes of the various embodiments described and/or illustrated herein. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program. The individual components of the various embodiments may be virtualized and hosted by a cloud type computational environment, for example to allow for dynamic allocation of computational power, without requiring the user concerning the location, configuration, and/or specific hardware of the computer system.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f), unless and until such claim limitations expressly use the phrase "means for" followed by a statement of function void of further structure.

This written description uses examples to disclose the various embodiments, and also to enable a person having ordinary skill in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A method of generating an image comprising:
   acquiring, with a computed tomography (CT) acquisition unit, CT projection data from at least a region of interest (ROI) of an object;
   acquiring, concurrently with acquiring the CT projection data, with a magnetic resonance (MR) acquisition unit, MR imaging information of at least a portion of the ROI;
   estimating a motion field within the at least a portion of the ROI using the MR imaging information; and
   reconstructing the image using the CT projection data, wherein reconstructing the image comprises motion correcting the CT projection data based on the motion estimated using the MR imaging information.

2. The method of claim 1, wherein the ROI comprises at least a portion of a heart.

3. The method of claim 1, wherein the ROI comprises the at least a portion of the ROI and at least one additional portion, further comprising estimating a motion of the at least one additional portion using the estimated motion of the at least a portion of the ROI.

4. The method of claim 1, wherein the acquiring the MR imaging information includes tagging the at least a portion of the ROI, wherein tagging comprises controlling a magnetic field to impose a grid pattern on the at least a portion of the ROI, and wherein estimating the motion of the at least a portion of the ROI comprises determining a deformation of the grid pattern.

5. The method of claim 4, wherein the at least a portion of the ROI comprises a myocardium of a heart.

6. The method of claim 5, further comprising estimating a motion of at least one additional portion of the heart using the estimated motion of the myocardium.

7. The method of claim 6, wherein the at least one additional portion of the heart comprises vessels disposed at least one of along or near a surface of the myocardium.

8. The method of claim 1, wherein the MR imaging information used for estimating the motion field is acquired at a resolution that is lower than a resolution of the image generated from the CT projection data.

9. A tangible and non-transitory computer readable medium comprising one or more computer software modules configured to direct one or more processors to:
   acquire computed tomography (CT) projection data of at least a region of interest (ROI) of an object;
   acquire, concurrently with acquiring the CT projection data, MR imaging information of at least a portion of the ROI;
   estimate a motion field within at least a portion of the ROI using the MR imaging information; and
   reconstruct the image using the CT projection data, wherein reconstructing the image comprises motion correcting the CT projection data based on the motion estimated using the MR imaging information.

10. The computer readable medium of claim 9, wherein the ROI comprises the at least a portion of the ROI and at least one additional portion, wherein the computer readable medium is further configured to direct the one or more processors to estimate a motion of the additional portions using the estimated motion of the at least a portion of the ROI.

11. The computer readable medium of claim 9, wherein the computer readable medium is further configured to direct the one or more processors to tag the at least a portion of the ROI, wherein tagging comprises controlling a magnetic field to impose a grid pattern on the at least a portion of the ROI, and wherein the computer readable medium is further configured to direct the one or more processors to estimate the motion of the at least a portion of the ROI using a determined deformation of the grid pattern.

12. The computer readable medium of claim 11, wherein the at least a portion of the ROI comprises a myocardium of a heart.

13. The computer readable medium of claim 12, wherein the computer readable medium is further configured to direct the one or more processors to estimate a motion of at least one additional portion of the heart using the estimated motion of the myocardium.

14. The computer readable medium of claim 9, wherein the computer readable medium is further configured to direct the one or more processors to acquire the MR imaging information, used for estimating the motion field, at a resolution that is lower than a resolution of the image generated from the CT projection data.

15. An imaging system comprising:
a computed tomography (CT) acquisition unit configured to acquire CT projection data of at least a region of interest (ROI) of an object, the CT acquisition unit having a CT field of view;
a magnetic resonance (MR) acquisition unit configured to acquire MR imaging information of at least a portion of the ROI concurrently with acquisition of the CT projection data by the CT acquisition unit, the MR acquisition unit having a MR field of view that at least partially overlaps with the CT field of view;
and a processing unit operably coupled to the CT acquisition unit and the MR acquisition unit, the processing unit configured to:
estimate a motion field of the at least a portion of the ROI using the MR imaging information; and
reconstruct an image using the CT projection data, wherein reconstructing the image comprises motion correcting the CT projection data based on the motion estimated using the MR imaging information.

16. The imaging system of claim 15, wherein the ROI comprises the at least a portion of the ROI and at least one additional portion, and wherein the processing unit is further configured to estimate a motion of the at least one additional portion using the estimated motion of the at least a portion of the ROI.

17. The imaging system of claim 15, wherein the processing unit is configured to control the MR acquisition unit to tag the at least a portion of the ROI, wherein tagging comprises controlling a magnetic field to impose a grid pattern on the at least a portion of the ROI, and wherein the processing unit is further configured to direct the one or more processors to estimate the motion of the at least a portion of the ROI using a determined deformation of the grid pattern.

18. The imaging system of claim 17, wherein the at least a portion of the ROI comprises a myocardium of a heart.

19. The imaging system of claim 18, wherein the processing unit is configured to estimate a motion of at least one additional portion of the heart using the estimated motion of the myocardium.

20. The imaging system of claim 15, wherein the processing unit is configured to control the MR acquisition unit to acquire the MR imaging information, used for estimating the motion field, at a resolution that is lower than a resolution of the image generated from projection data acquired by CT acquisition unit.

* * * * *